US006428993B1

(12) United States Patent
Bech et al.

(10) Patent No.: US 6,428,993 B1
(45) Date of Patent: *Aug. 6, 2002

(54) TRANSGLUTAMINASE FROM OOMYCETES

(75) Inventors: Lisbeth Bech; Grethe Rasmussen; Torben Halkier, all of Bagsvaerd (DK); Mariko Okada, Chiba (JP); Lene Nonboe Andersen, Bagsvaerd (DK); Markus Sakari Kauppinen, Bagsvaerd (DK); Thomas Sandal, Bagsvaerd (DK)

(73) Assignee: Novozymes A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/881,742

(22) Filed: Jun. 24, 1997

Related U.S. Application Data

(63) Continuation of application No. PCT/DK96/00031, filed on Jan. 19, 1996.

(30) Foreign Application Priority Data

Jan. 19, 1995 (DK) ............................................... 0061/95

(51) Int. Cl.$^7$ ............................ C12N 9/10; C12N 15/54
(52) U.S. Cl. .................... 435/193; 435/251.1; 435/911; 536/23.2
(58) Field of Search ............... 435/193, 251.1, 435/911, 153, 251; 536/23.2

(56) References Cited

U.S. PATENT DOCUMENTS 4,054,595 A * 10/1977 Marx et al. ................. 560/121
4,687,744 A * 8/1987 Kerwin et al. .............. 435/242
5,514,573 A * 5/1996 Yasueda et al. ............. 435/193

FOREIGN PATENT DOCUMENTS

| EP | 0 481 504 | 4/1992 |
| JP | 6-78783 | 3/1994 |
| WO | WO 89/07398 | 8/1989 |

OTHER PUBLICATIONS

Green et al. The isolation and structure of 23–deoxyantherdiol and the synthesis of its C–22 epimer. Tetrahedron 27:1199–1203, 1971.*
Sacks, W et al, Mol. Gen. Genet vol. 246; pp. 45–55 (1995).
Klein, J. D. et al., Journal of Bacteriology, 1992, pp. 2599–2605.
Tomita K, et al., Agric. Biol. Chem., vol. 52 (9), pp. 2373–2374 (1988).
Tomita K, et al., Agric. Biol. Chem., vol. 53(12), pp. 3239–3244 (1989).

* cited by examiner

Primary Examiner—Gabrielle Bugaisky
(74) Attorney, Agent, or Firm—Elias J. Lambiris; Jason Garbell

(57) ABSTRACT

The present invention relates to transglutaminases and transglutaminase preparations obtained from lower fungi belonging to the class Oomycetes. Unprecedented high-level expression is achievable by growing these coenocytium forming organisms, especially the strains Pythium sp., Pythium irregulare, Pythium dissotocum, Pythium periilum (or P. periplocum), Pythium torulosum, Pythium ultimum, Pythium aphanidermatum, Phytophthora cactorum, Phytophthora palmivora, Phytophthora porri, Phytophthora infestans, Phytoph-thora megasperma, Phytophthora cinnamomi and Phytophthora cryptogea. Arecombinant transglutaminase has been cloned and expressed, the enzyme and enzyme preparations being useful for cross-linking proteins, e.g. in flour, baked products, meat products, fish products, cosmetics, cheese, milk products, gelled food products and leather finishing, or as a glutaminase, e.g. in bread and other baked glutein-containing food products.

5 Claims, No Drawings

TRANSGLUTAMINASE FROM OOMYCETES

CROSS-REFERENCE TO RELATED APPLICATIONS

This application is a continuation applications of serial no. PCT/DK96/00031 filed Jan. 19, 1996 and claims priority under 35 U.S.C. 119 of Danish application serial no. 0061/95 filed Jan. 19, 1995, the contents of which are fully incorporated herein by reference.

BACKGROUND OF THE INVENTION

1. Field of the Invention

The present invention relates to novel transglutaminase preparations derivable from the class Oomycetes, a novel transglutaminase derived from *Phytophthora cactorum*, CBS 618.94 or IFO 30474, a DNA construct encoding the transglutaminase enzyme, a method of producing the novel transglutaminase and the novel transglutaminase preparation, a method for producing a gel or protein gelation composition, and the use thereof.

2. Description of Related Art

Transglutaminases are enzymes capable of catalyzing an acyl transfer reaction in which a gamma-carboxyamide group of a peptide-bound glutamine residue is the acyl donor. Primary amino groups in a variety of compounds may function as acyl acceptors with the subsequent formation of monosubstituted gamma-amides of peptide-bound glutamic acid. When the ε-amino group of a lysine residue in a peptide-chain serves as the acyl acceptor, the transglutaminases form intramolecular or intermolecular ε-(γ-Glu)-Lys crosslinks.

This peptide crosslinking activity is useful for a variety of industrial purposes, including gelling of proteins, reduction of antigenicity of proteins, improvement of baking quality of flour, producing paste type food materia from protein, fat and water, preparation of cheese from milk concentrate, binding of chopped meat product, improvement of taste and texture of food proteins, producing jelly, gel cosmetics etc.

A wide array of transglutaminases have been isolated and characterized from animals and plants. The animal derived TGases are $Ca^{2+}$-dependent and often multi-subunit enzymes. The most widely used mammalian transglutaminase, FXIIIa, is product inhibited, difficult to obtain in high amounts and thus expensive, and therefore not useful for all applications.

A few microbial TGases have been described, including the $Ca^{2+}$-independent TGases from Streptoverticillia disclosed in U.S. Pat. No. 5,156,956 and related species disclosed in U.S. Pat. No. 5,252,469.

The yields of the microbial transglutaminases in shake-flasks and fermentors are far below those seen for other industrial enzymes. Thus, better production methods, including new high-yielding producers are needed. Previously, this goal has been pursued by applying conventional recombinant DNA techniques for cloning and expression in *E. coli*, *S. cerevisiae* and *S. lividans* (Washizu et al.; Tahekana et al.; Takagi et al.) but without success.

Klein et al. found and partially characterized a transglutaminase from the slime mold *Physarum polycephalum* which is a homodimer having a total molecular weight of 77 kDa. JP 6078783 Kokai relates to the use of this transglutaminase for protein gelation. However, it is well-known that slime molds are unsuited for large-scale industrial fermentation. Further, Physarum is not a fungus; it belongs to the Myxomycetes (Entrez NIH data base, current version January 1996). Taxonomically, the only common feature of Oomycetes, Myxomycetes and Eumycota (fungi) is that they all are mitochondrial eukaryotes.

The object of the invention is to provide a novel transglutaminase, a novel transglutaminase preparation, a method for producing the transglutaminase or transglutaminase preparation in a better yield and higher purity than hitherto possible which transglutaminase can be used either alone or in combination with other enzymes for industrial purposes.

SUMMARY OF THE INVENTION

Surprisingly, it has been found that organisms belonging to the class Oomycetes produce transglutaminase and that high-level expression is achievable by growing these coenocytium forming organisms.

In particular, isolates belonging to the class Oomycetes have been shown to express transglutaminases in unprecedented high amounts, including isolates belonging to the order Peronosporales, family Pythiaceae, and the genera Pythium and Phytophthora.

Accordingly, the present invention relates to transglutaminase preparations producible by cultivation of a transglutaminase producing strain of the class Oomycetes and to novel transglutaminases derived from transglutaminase producing strains of the class Oomycetes. Preferably, the novel transglutaminase and the transglutaminase preparation of the invention are derived from or producible by transglutaminase producing strains belonging to the class Oomycetes.

Further, the present invention relates to a parent transglutaminase derived from or producible by a species selected from *Phytophthora cactorum*, CBS 618.94 or IFO 30474, *Phytophthora cryptogea*, CBS 651.94, *Pythium periilum* (or *P. periplocum*), CBS 620.94, *Pythium irregulars*, CBS 701.95, Pythium sp., CBS 702.95, *Pythium intermedium*, CBS 703.95, Pythium sp., CBS 704.95, *Pythium ultimum*, CBS 705.95 or a functional analogue thereof.

The present invention also relates to a method for the production of a transglutaminase preparation according to the invention by cultivating, in a suitable medium, a strain belonging to the class Oomycetes, preferably belonging to an order selected from Peronosporales, Saprolegniales, Leptomitales and Lagenidiales, more preferably belonging to a family selected from Pythiaceae, Peronosporaceae, Saprolegniaceae, Leptomitaceae, Rhiphidiaceae and Lagenidiaceae, especially belonging to a genus selected from Pythium and Phytophthora.

Further, the present inventors have now surprisingly succeeded in isolating and characterizing a DNA sequence from a strain of the oomycetes *Phytophthora cactorum* exhibiting transglutaminase activity, thereby making it possible to prepare a recombinant transglutaminase.

Accordingly, in yet another aspect the invention relates to a DNA construct comprising a DNA sequence encoding an enzyme exhibiting transglutaminase activity, which DNA sequence comprises a) the DNA sequence shown in SEQ ID No. 1, and/or the DNA sequence obtainable from the plasmid in *Escherichia coli* DSM 10256 or b) an analogue of the DNA sequence shown in SEQ ID No. 1 and/or the DNA sequence obtainable from the plasmid in *Escherichia coli* DSM 10256, which i) is homologous with the DNA sequence shown in SEQ ID No. 1 and/or the DNA sequence obtainable from the plasmid in *Escherichia coli* DSM 10256, or ii) hybridizes with the same oligonucleotide probe as the DNA sequence shown in SEQ ID No. 1 and/or the DNA sequence obtainable from the plasmid in *Eschefichia coli* DSM 10256, or iii) encodes a polypeptide which is homologous with the polypeptide encoded by a DNA sequence comprising the DNA sequence shown in SEQ ID No. 1 and/or the DNA sequence obtainable from the plasmid in *Escherichia coli* DSM 10256, or iv) encodes a polypeptide which is immunologically reactive with an antibody raised against the purified transglutaminase encoded by the DNA sequence shown in SEQ ID No 1 and/or the DNA sequence obtainable from the plasmid in *Escherichia coli* DSM 10256.

It is believed that the DNA sequence shown in SEQ ID No. 1 is identical to the DNA sequence obtainable from the plasmid in *Escherichia coli* DSM 10256.

The strain *Escherichia coli* was deposited under the deposition number DSM 10256 on Sep. 18, 1995 at the DSM—Deutsche Sammlung von Mikroorganismen und Zellkulturen GmbH, Maascheroder Weg 1b, D-38125 Braunschweig, Germany, according to the Budapest Treaty.

In another aspect, the invention relates to a method of crosslinking proteins comprising contacting a proteinaceous substrate with a transglutaminase or transglutaminase preparation of the present invention.

In yet another aspect, the invention relates to use of the transglutaminase or transglutaminase preparation of the present invention in flour, baked products, meat products, fish products, cosmetics, cheese, milk products, gelled food products and leather finishing.

DETAILED DESCRIPTION OF THE INVENTION

In the present specification and claims, the term "transglutaminase" is intended to be understood as an enzyme capable of catalyzing an acyl transfer reaction in which a gamma-carboxyamide group of a peptide-bound glutamine residue is the acyl donor.

In the present context the term "derivable" or "derived from" is intended not only to indicate a transglutaminase produced by a strain of the organism in question, but also a transglutaminase encoded by a DNA sequence isolated from such strain and produced in a host organism transformed with said DNA sequence. Furthermore, the term is intended to indicate a transglutaminase which is encoded by a DNA sequence of synthetic and/or cDNA origin and which has the identifying characteristics of the transglutaminase in question.

The transglutaminase may be a component occurring in an enzyme system produced by a given microorganism, such an enzyme system mostly comprising several different enzyme components. In the present specification and claims, such an enzyme system comprising at least one transglutaminase component is denoted "transglutaminase preparation".

Alternatively, the transglutaminase may be a single component, i.e. a component essentially free of other enzyme components usually occurring in an enzyme system produced by a given microorganism, the single component being a recombinant component, i.e. produced by cloning of a DNA sequence encoding the single component and subsequent cell transformed with the DNA sequence and expressed in a host. The host is preferably a heterologous host, but the host may under certain conditions also be the homologous host. A recombinant transglutaminase may be cloned and expressed according to standard techniques conventional to the skilled person.

According to the present invention, the native or unmodified transglutaminase is of microbial origin, more specifically obtainable from a strain belonging to the class Oomycetes.

The class Oomycetes comprises the orders Peronosporales, Saprolegniales, Leptomitales and Lagenidiales.

The order Peronosporales comprises the families Pythiaceae, Peronosporaceae, Peronophytophthoraceae and Albuginaceae.

The order Saprolegniales comprises the families Saprolegniaceae, Ectrogellaceae, Thraustochytriaceae, Haliphthoraceae and Leptolegniellaceae.

The order Leptomitales comprises the families Leptomitaceae and Rhiphidiaceae.

The order Lagenidiales comprises the families Lagenidiaceae, Olpidiaceae and Sirolpidiaceae.

It is contemplated that all orders and all families taxonomically belonging to the class Oomycetes comprise transglutaminase producing strains. In this respect it should be noted that the families Peronophytophthoraceae, Albuginaceae, Ectrogellaceae, Thraustochytriaceae, Haliphthoraceae, Leptolegniellaceae, Olpidiaceae and Sirolpidiaceae are small and often highly specialised. Thus, the families Pythiaceae, Peronosporaceae, Saprolegniaceae, Leptomitaceae, Rhiphidiaceae and Lagenidiaceae should be considered as being representative of the Oomycetes.

In a preferred embodiment, the transglutaminase preparation of the present invention is producible by a transglutaminase producing strain which taxonomically belongs to the family Pythiaceae, preferably to the genus Pythium or the genus Phytophthora, more preferably to a subdivision of the genus Pythium Pringsheim (Waterhouse) or a subdivision of the genus Phytophthora deBary (Newhook, Waterhouse and Stamps). In the following, examples of members of all subdivisions (I–III) of genus Pythium, and all subdivisions (I–VI) of genus Phytophthora are given. Examples of transglutaminase producing species of the genus Pythium are I) *P. irregulars*, CBS 701.95;

IIA$_1$) *P. dissotocum;*

IIA$_2$) *P. periilum* (or *P. pefiplocum*); *P. torulosum; P. aphanidennatum;* preferably *P. periilum* (or *P. periplocum*), CBS 620.94;

IIB) *P. ultimum*, CBS 705.95;

III) *P. intermedium*, CBS 703.95.

Examples of transglutaminase producing species of the genus Phytophthora are

I) *P. cactorum;* preferably *P. cactorum*, CBS 618.94 and IFO 30474.

II) *P. palmivora;*

III) *P. porri;*

IV) *P. infestans;*

V) *P. megaspenna;*

VI) *P. cryptogea;* and *P. cinnamomi;* preferably *P. cryptogea*, CBS 651.94.

In another preferred embodiment, the transglutaminase preparation of the present invention is producible by a transglutaminase producing strain which taxonomically belongs to the family Peronosporaceae, preferably to the genus Plasmopara, more preferably to the species *Plasmopara halstedii*.

In yet another preferred embodiment, the transglutaminase preparation of the present invention is producible by a transglutaminase producing strain which taxonomically belongs to the family Saprolegniaceae, preferably to a genus selected from the genera Achlya, Saprolegnia and Aphanoniyces.

In yet another preferred embodiment, the transglutaminase preparation of the present invention is producible by a transglutaminase producing strain which taxonomically belongs to the family Leptomitaceae, preferably to a genus selected from the genera Apodachlya and Leptomitus.

In yet another preferred embodiment, the transglutaminase preparation of the present invention is producible by a transglutaminase producing strain which taxonomically belongs to the family Rhiphidiaceae, preferably to a genus selected from the genera Aqualinderella and Rhiphidium.

In yet another preferred embodiment, the transglutaminase preparation of the present invention is producible by a transglutaminase producing strain which taxonomically belongs to the family Lagenidiaceae, preferably to a genus selected from the genera Lagenidium and Olpidiopsis.

In a preferred aspect of the invention, it is contemplated that novel transglutaminases are obtainable by or derivable from species selected from the group of genera consisting of Pythium and Phytophthora, more preferably from the species *Pythium periilum* (or *P. periplocum*), *Pythium irregulars*, Pythium sp., *Pythium ultimum, Pythium intermedium, Phytophthora cactorum* and *Phytophthora cryptogea*, especially from the species *Pythium periilum* (or *P. periplocum*) deposited at Centraalbureau voor Schimmelcultures, Oosterstraat 1, NL-3742 SK Baarn, The Netherlands on Dec. 20, 1994 under the deposition number CBS 620.94; *Phytophthora cactorum* deposited at Centraalbureau voor Schimmelcultures under the deposition number CBS 618.94 on Dec. 20, 1994 (and redeposited on Oct. 19, 1995) and previously at the Institute for Fermentation, Osaka, under the deposition number IFO 30474; *Phytophthora cryptogea* deposited at Centraalbureau voor Schimmelcultures on Dec. 27, 1994 under the deposition number CBS 651.94; *Pythium irregulare* deposited at Centraalbureau voor Schimmelcultures on Oct. 19, 1995 under the deposition number CBS 701.95; Pythium sp. deposited at Centraalbureau voor Schimmelcultures on Oct. 19, 1995 under the deposition number CBS 702.95; *Pythium internedium* deposited at Centraalbureau voor Schimmelcultures on Oct. 19, 1995 under the deposition number CBS 703.95; Pythium sp. deposited at Centraalbureau voor Schimmelcultures on Oct. 19, 1995 under the deposition number CBS 704.95; *Pythium ultimum* deposited at Centraalbureau voor Schimmelcultures on Oct. 19, 1995 under the deposition number CBS 705.95; all depositions made under the Budapest Treaty.

The transglutaminase component may be derived either from the homologous or a heterologous host. Preferably, the component is homologous. However, a heterologous component which is immunologically reactive with an antibody raised against a highly purified transglutaminase and which is derived from a specific microorganism is also preferred.

Advantageously, a parent transglutaminase derivable from a strain of the genera Pythium and Phytophthora may be used.

In a preferred embodiment, the parent transglutaminase is selected from the group consisting of a *Phytophthora cactorum*, CBS 618.94/IFO 30474, transglutaminase; a *Pythium pertilum* (or *P. periplocum*), CBS 620.94, transglutaminase; a *Pythium irregulars*, CBS 701.95, transglutaminase; a Pythium sp., CBS 702.95, transglutaminase; a *Pythium intermedium*, CBS 703.95, transglutaminase; a Pythium sp., CBS 704.95, transglutaminase; a *Pythium ultimum*, CBS 705.95, transglutaminase and a *Phytophthora cryptogea*, CBS 651.94, transglutaminase; or is a functional analogue of any of said parent transglutaminases which (i) comprises an amino acid sequence being at least 40%, preferably at least 60%, especially more than 74%, homologous with the amino acid sequence of the parent transglutaminase, (ii) reacts with an antibody raised against the parent transglutaminase, and/or (iii) is encoded by a DNA sequence which hybridizes with the same probe as a DNA sequence encoding the parent transglutaminase.

Property i) of the analogue is intended to indicate the degree of identity between the analogue and the parent transglutaminase indicating a derivation of the first sequence from the second. In particular, a polypeptide is considered to be homologous to the parent transglutaminase if a comparison of the respective amino acid sequences reveals an identity of greater than about 40%, such as above 45%, 50%, 55%, 60%, 65%, 70%, 74%, 80%, 85%, 90% or even 95%. Sequence comparisons can be performed via known algorithms, such as the one described by Lipman and Pearson (1985).

The additional properties ii) and iii) of the analogue of the parent transglutaminase may be determined as follows:

Property ii), i.e. the immunological cross reactivity, may be assayed using an antibody raised against or reactive with at least one epitope of the parent transglutaminase.

The antibody, which may either be monoclonal or polyclonal, may be produced by methods known in the art, e.g. as described by Hudson et al., 1989. The immunological cross-reactivity may be determined using assays known in the art, examples of which are Western Blotting or radial immunodiffusion assay, e.g. as described by Hudson et al., 1989.

The probe used in the characterization of the analogue in accordance with property iii) defined above, may suitably be prepared on the basis of the full or partial nucleotide or amino acid sequence of the parent transglutaminase. The hybridization may be carried out under any suitable conditions allowing the DNA sequences to hybridize. For instance, such conditions are hybridization under specified conditions, e.g. involving presoaking in 5×SSC and prehybridizing for 1 h at ~45° C. in a solution of 5×SSC, 5×Denhardt's solution, 0.5% SDS, and 100 $\mu$g/ml of denatured sonicated salmon sperm DNA, followed by hybridization in the same solution supplemented with $^{32}$P-dCTP-labelled probe for 12 h at ~45° C., or other methods described by e.g. Sambrook et al., 1989.

In the present context, the "analogue" of the DNA sequence shown in SEQ ID No. 1 is intended to indicate any DNA sequence encoding an enzyme exhibiting transglutaminase activity, which has any or all of the properties i)–iv) of claim 27. The analogous DNA sequence a) may be isolated from another or related (e.g. the same) organism producing the enzyme with transglutaminase activity on the basis of the DNA sequence shown in SEQ ID No. 1, e.g. using the procedures described herein, and thus, e.g. be an allelic or species variant of the DNA sequence comprising the DNA sequences shown herein, b) may be constructed on the basis of the DNA sequence shown in SEQ ID No. 1, e.g. by introduction of nucleotide substitutions which do not give rise to another amino acid sequence of the transglutaminase encoded by the DNA sequence, but which correspond to the codon usage of the host organism intended for production of the enzyme, or by introduction of nucleotide substitutions which may give rise to a different amino acid sequence. However, in the latter case amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a polyhistidine tract, an antigenic epitope or a binding domain. See in general Ford et al., *Protein Expression and Purification* 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, *Science* 244, 1081–1085, 1989). In the latter technique mutations are introduced at every residue in the molecule, and the resultant mutant molecules are tested for biological (i.e. transglutaminase) activity to identify amino acid residues that are critical to the activity of the molecule. Sites of substrate-enzyme interaction can also be determined by analysis of crystal structure as determined by such techniques as nuclear magnetic resonance, crystallography or photoaffinity labeling. See, for example, de Vos et al., *Science* 255: 306–312, 1992; Smith et al., *J. Mol. Biol.* 224: 899–904, 1992; Wlodaver et al., *FEBS Lett.* 309: 59–64, 1992.

The homology referred to in i) above or of claim 27 is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for DNA sequence comparison: GAP creation penalty of 5.0 and GAP extension penalty of 0.3, the coding region of the DNA sequence exhibits a degree of identity preferably of at least 40%, more preferably at least 50%, more preferably at least 60%, more preferably at least 70%, more preferably at least 74%, even more preferably at least 80%, especially at least 90%, with the coding region of the DNA sequence shown in SEQ ID No.1.

The hybridization referred to in ii) above or of claim 27 is intended to indicate that the analogous DNA sequence hybridizes to the same probe as the DNA sequence encoding the transglutaminase enzyme under certain specified conditions which are described in detail in the Materials and Methods section hereinafter. Normally, the analogous DNA sequence is highly homologous to the DNA sequence such as at least 70% homologous to the DNA sequence shown in SEQ ID No. 1 encoding an transglutaminase of the invention, such as at least 75%, at least 80%, at least 85%, at least 90% or even at least 95% homologous to said DNA sequence.

The homology referred to in iii) above or of claim 27 is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for polypeptide sequence comparison: GAP creation penalty of 3.0 and GAP extension penalty of 0.1, the polypeptide encoded by a homologous DNA sequence exhibits a degree of identity preferably of at least 70%, more preferably at least 75%, most preferably at least 80%, especially at least 90%, with the enzyme encoded by a DNA construct comprising the DNA sequence shown in SEQ ID No. 1.

In connection with property iv) above or of claim 27 it is intended to indicate a transglutaminase encoded by a DNA sequence isolated from strain CBS 618.94 and produced in a host organism transformed with said DNA sequence or produced by the strain CBS 618.94. The immunological reactivity may be determined by the method described in the Materials and Methods section below.

In further aspects the invention relates to an expression vector harbouring a DNA construct of the invention, a cell comprising the DNA construct or expression vector and a method of producing an enzyme exhibiting transglutaminase activity which method comprises culturing said cell under conditions permitting the production of the enzyme, and recovering the enzyme from the culture.

In a still further aspect the invention relates to an enzyme exhibiting transglutaminase activity, which enzyme a) is encoded by a DNA construct of the invention b) produced by the method of the invention, and/or c) is immunologically reactive with an antibody raised against a purified transglutaminase encoded by the DNA sequence shown in SEQ ID No. 1.

The transglutaminase mentioned in c) above may be encoded by the DNA sequence isolated from the strain *Phytophthora cactorum*, CBS 618.94, and produced in a host organism transformed with said DNA sequence or produced by the strain CBS 618.94.

The DNA sequence of the invention encoding an enzyme exhibiting transglutaminase activity may be isolated by a general method involving cloning, in suitable vectors, a DNA library from *Phytophthora cactorum*, transforming suitable yeast host cells with said vectors, culturing the host cells under suitable conditions to express any enzyme of interest encoded by a clone in the DNA library, screening for positive clones by determining any transglutaminase activity of the enzyme produced by such clones, and isolating the enzyme encoding DNA from such clones.

The general method is further disclosed in WO 94/14953 the contents of which are hereby incorporated by reference. A more detailed description of the screening method is given in Example 5 below.

The DNA sequence coding for the enzyme may for instance be isolated by screening a cDNA library of *Phy-* tophthora cactorum, and selecting for clones expressing transglutaminase activity, or from *Escherichia coli*, DSM 10256. The appropriate DNA sequence may then be isolated from the clone by standard procedures, e.g. as described in Example 5.

It is expected that a DNA sequence coding for a homologous enzyme, i.e. an analogous DNA sequence, is obtainable from other microorganisms. For instance, the DNA sequence may be derived by similarly screening a cDNA library of another fungus, such as a strain of Pythium.

Alternatively, the DNA coding for a transglutaminase of the invention may, in accordance with well-known procedures, conveniently be isolated from DNA from a suitable source, such as any of the above mentioned organisms, by use of synthetic oligonucleotide probes prepared on the basis of a DNA sequence disclosed herein. For instance, a suitable oligonucleotide probe may be prepared on the basis of the nucleotide sequence shown in SEQ ID No. 1 or any suitable subsequence thereof.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the transglutaminase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the transglutaminase, the promoter and the terminator, respectively, and to insert them into suitable vectors are well known to persons skilled in the art (cf., for instance, Sambrook et al., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus or Trichodenna, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces, in particular *Saccharomyces cerevisiae, Saccharomyces kluyveri* or *Saccharomyces uvarum*, a strain of Schizosaccharomyces sp., such as *Schizosaccharomyces pombe*, a strain of Hansenula sp. Pichia sp., Yarrowia sp. such as *Yarrowia lipolytica*, or Kluyveromyces sp. such as *Kluyveromyces lactis*.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed transglutaminase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Cloning and Expression of a Transglutaminase Enzyme from *Phytophthora cactorum*

MATERIALS AND METHODS
Deposited organism:
*Escherichia coli* DSM 10256 containing the plasmid comprising the full length DNA sequence, coding for the transglutaminase of the invention, in the shuttle vector pYES 2.0.
Yeast Strain:
The Saccharomyces cerevisiae strain used was W3124 (MATα; ura 3–52; leu 2–3, 112; his 3-D200; pep 4–1137; prc1::HIS3; prb1:: LEU2; cir+).

Plasmids:
The Aspergillus expression vector pHD414 is a derivative of the plasmid p775 (described in EP 238 023). The construction of pHD414 is further described in WO 93/11249.

pYES 2.0 (Invitrogen)
Isolation of the DNA Sequence Shown in SEQ ID No. 1:
The full length DNA sequence, comprising the cDNA sequence shown in SEQ ID No. 1 coding for the transglutaminase of the invention, can be obtained from the deposited organism *Escherichia coli* DSM 10256 by extraction of plasmid DNA by methods known in the art (Sambrook et al.).
Extraction of total RNA was performed with guanidinium thiocyanate followed by ultracentrifugation through a 5.7 M CsCl cushion, and isolation of poly(A)$^+$RNA was carried out by oligo(dT)-cellulose affinity chromatography using the procedures described in WO 94/14953.
cDNA Synthesis:
Double-stranded cDNA was synthesized from 5 μg poly (A)$^+$RNA by the RNase H method (Gubler and Hoffman, Sambrook et al.) using the hair-pin modification developed by F. S. Hagen (pers. comm.). The poly(A)$^+$RNA (5 μg in 5 μl of DEPC-treated water) was heated at 70° C. for 8 min. in a pre-siliconized, RNase-free Eppendorp tube, quenched on ice and combined in a final volume of 50 μl with reverse transcriptase buffer (50 mM Tris-Cl, pH 8.3, 75 mM KCl, 3 mM MgCl$_2$, 10 mM DTT, Bethesda Research Laboratories) containing 1 mM of dATP, dGTP and dTTP and 0.5 mM 5-methyl-dCTP (Pharmacia), 40 units human placental ribonuclease inhibitor (RNasin, Promega), 1.45 μg of oligo(dT)$_{18}$-Not I primer (Pharmacia) and 1000 units SuperScript II RNase H reverse transcriptase (Bethesda Research Laboratories). First-strand cDNA was synthesized by incubating the reaction mixture at 45° C. for 1 hour. After synthesis, the mRNA:cDNA hybrid mixture was gelfiltrated through a MicroSpin S-400 HR (Pharmacia) spin column according to the manufacturer's instructions.
After the gelfiltration, the hybrids were diluted in 250 μl second strand buffer (20 mM Tris-Cl, pH 7.4, 90 mM KCl, 4.6 mM MgCl$_2$, 10 mM (NH$_4$)$_2$SO$_4$, 0.16 mM βNAD+) containing 200 μM of each dNTP, 60 units *E. coli* DNA polymerase I (Pharmacia), 5.25 units RNase H (Promega) and 15 units *E. coli* DNA ligase (Boehringer Mannheim).

Second strand cDNA synthesis was performed by incubating the reaction tube at 16° C. for 2 hours and additional 15 min. at 25° C. The reaction was stopped by addition of EDTA to a final concentration of 20 mM followed by phenol and chloroform extractions.

Mung bean Nuclease Treatment:

The double-stranded cDNA was precipitated at −20° C. for 12 hours by addition of 2 vols 96% EtOH, 0.2 vol 10 M $NH_4Ac$, recovered by centrifugation, washed in 70% EtOH, dried and resuspended in 30 µl Mung bean nuclease buffer (30 mM NaAc, pH 4.6, 300 mM NaCl, 1 mM $ZnSO_4$, 0.35 mM DTT, 2% glycerol) containing 25 units Mung bean nuclease (Pharmacia). The single-stranded hair-pin DNA was clipped by incubating the reaction at 30° C. for 30 min., followed by addition of 70 µl 10 mM Tris-Cl, pH 7.5, 1 mM EDTA, phenol extraction and precipitation with 2 vols of 96% EtOH and 0.1 vol 3 M NaAc, pH 5.2 on ice for 30 min.

Blunt-ending with T4 DNA Polymerase:

The double-stranded cDNAs were recovered by centrifugation and blunt-ended in 30 µl T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs) by incubating the reaction mixture at 16° C. for 1 hour. The reaction was stopped by addition of EDTA to a final concentration of 20 mM, followed by phenol and chloroform extractions, and precipitation for 12 hours at −20° C. by adding 2 vols 96% EtOH and 0.1 vol 3 M NaAc pH 5.2.

Adaptor Ligation, Not I Digestion and Size Selection:

After the fill-in reaction the cDNAs were recovered by centrifugation, washed in 70% EtOH and dried. The cDNA pellet was resuspended in 25 µl ligation buffer (30 mM Tris-Cl, pH 7.8, 10 mM $MgCl_2$, 10 mM DTT, 0.5 mM ATP) containing 2.5 µg non-palindromic BstXI adaptors (Invitrogen) and 30 units T4 ligase (Promega) and incubated at 16° C. for 12 hours. The reaction was stopped by heating at 65° C. for 20 min. and then cooling on ice for 5 min. The adapted cDNA was digested with Not I restriction enzyme by addition of 20 µl water, 5 µl 10× Not I restriction enzyme buffer (New England Biolabs) and 50 units Not I (New England Biolabs), followed by incubation for 2.5 hours at 37° C. The reaction was stopped by heating at 65° C. for 10 min. The cDNAs were size-fractionated by gel electrophoresis on a 0.8% SeaPlaque GTG low melting temperature agarose gel (FMC) in 1×TBE to separate unligated adaptors and small cDNAs. The cDNA was size-selected with a cut-off at 0.7 kb and rescued from the gel by use of β-Agarase (New England Biolabs) according to the manufacturer's instructions and precipitated for 12 hours at −20° C. by adding 2 vols 96% EtOH and 0.1 vol 3 M NaAc pH 5.2.

Construction of Libraries:

The directional, size-selected cDNA was recovered by centrifugation, washed in 70% EtOH, dried and resuspended in 30 µl 10 mM Tris-Cl, pH 7.5, 1 mM EDTA. The cDNAs were desalted by gelfiltration through a MicroSpin S-300 HR (Pharmacia) spin column according to the manufacturer's instructions. Three test ligations were carried out in 10 µl ligation buffer (30 mM Tris-Cl, pH 7.8, 10 mM $MgCl_2$, 10 mM DTT, 0.5 mM ATP) containing 5 µl double-stranded cDNA (reaction tubes #1 and #2), 15 units T4 ligase (Promega) and 30 ng (tube #1), 40 ng (tube #2) and 40 ng (tube #3, the vector background control) of BstXI-NotI cleaved pYES 2.0 vector. The ligation reactions were performed by incubation at 16° C. for 12 hours, heating at 70° C. for 20 min. and addition of 10 µl water to each tube. 1 µl of each ligation mixture was electroporated into 40 µl electrocompetent E. coli DH10B cells (Bethesda research Laboratories) as described (Sambrook et al.). Using the optimal conditions a library was established in E. coli consisting of pools containing 15.000–30.000 colony forming units. Each pool of transformed E. coli was spread on LB+ampicillin agar plates giving 15.000–30.000 colonies/ plate after incubation at 37° C. for 24 hours. 20 ml LB+ampicillin was added to the plate and the cells were suspended herein. The cell suspension was shaked in a 50 ml tube for 1 hour at 37° C. Plasmid DNA was isolated from the cells according to the manufacturer's instructions using QIAGEN plasmid kit and stored at −20° C.

1 µl aliquots of purified plasmid DNA (100 ng/µl) from individual pools were transformed into S. cerevisiae W3124 by electroporation (Becker and Guarante) and the transformants were plated on SC agar containing 2% glucose and incubated at 30° C.

Identification of positive colonies:

After 3–5 days of growth, the agar plates were replica plated onto a set of SC-variant agar plates. These plates were incubated for 6–8 days at 30° C.

Round (diameter 8.2 cm) Immobilon PVDF Transfer Membranes for protein blotting (Millipore) were wetted for 1–3 seconds in 96% EtOH and rinsed in water for 1 min. The membranes were incubated for 2 hours in 2% N,N-dimethylcasein, 150 mM NaCl, 0.1 M Trisbuffer pH 7.5 and washed twice (1 min.) in 150 mM NaCl, 0.1 M Trisbuffer pH 7.5.

A casein saturated membrane was placed on each SC-variant agar plate with yeast colonies. The plate was incubated at 30° C. over night with 1 ml 0.5 mM 5-(biotinamido)-pentylamine (Pierce), 0.1 M Trisbuffer pH 7.5, 50 mM $CaCl_2$. After 3 washes (15 min.) in 0.1 M $Na_3PO_4/H_3PO_4$ buffer pH 6.5 the membrane was incubated for 1 hour at room temperature with 10 ml 0.17 µg/ml peroxidase-labeled Streptavidin (Kirkegaard & Perry Laboratories Inc.). After further 3 washes (15 min.) in 0.1 M $Na_3PO_4/H_3PO_4$ buffer pH 6.5 the membrane was incubated at room temperature with 1 ml 2 mM ABTS (Sigma), 1 mM $H_2O_2$, 0.1 M $Na_3PO_4/H_3PO_4$ buffer pH 6.5 until transglutaminase positive colonies were identified by a green or lilac zone.

Cells from enzyme-positive colonies were spread for single colony isolation on agar, and an enzyme-producing single colony was selected for each of the transglutaminase-producing colonies identified.

Characterization of Positive Clones:

The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al.) and the Sequenase system (United States Biochemical).

Isolation of a cDNA Gene for Expression in Aspergillus:

A transglutaminase-producing yeast colony was inoculated into 20 ml YPD broth in a 50 ml glass test tube. The tube was shaken for 2 days at 30° C. The cells were harvested by centrifugation for 10 min. at 3000 rpm.

DNA was isolated according to WO 94/14953 and dissolved in 50 µl water. The DNA was transformed into E. coli by standard procedures. Plasmid DNA was isolated from E. coli using standard procedures, and analyzed by restriction enzyme analysis. The cDNA insert was excised using appropriate restriction enzymes and ligated into an Aspergillus expression vector.

Transformation of *Aspergillus oryzae* or *Aspergillus niger*

Protoplasts may be prepared as described in WO 95/02043, p. 16, line 21—page 17, line 12.

100 μl of protoplast suspension is mixed with 5–25 μg of the appropriate DNA in 10 μl of STC (1.2 M sorbitol, 10 mM Tris-HCl, pH=7.5, 10 mM CaCl$_2$). Protoplasts are mixed with p3SR2 (an *A. nidulans* amdS gene carrying plasmid). The mixture is left at room temperature for 25 minutes. 0.2 ml of 60% PEG 4000 (BDH 29576), 10 mM CaCl$_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on minimal plates (Cove) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of A. Oryzae Transformants

Each of the transformants were inoculated in 10 ml YPM and propagated. After 2–5 days of incubation at 37° C., 10 ml supernatant was removed. The transglutaminase activity was identified by the 5-(biotinamido)-pentylamine plate assay described above and the Putrescine assay described in Example 1 below.

Hybridization conditions (to be used in evaluating property ii) of the DNA construct of the invention):

Suitable conditions for determining hybridization between a DNA or RNA or an oligonucleotide probe and a homologous DNA or RNA sequence involves presoaking of the filter containing the DNA fragments or RNA to hybridize in 5×SSC (standard saline citrate) for 10 min. and prehybridizing of the filter in a solution of 5×SSC (Sambrook et al., 1989), 5×Denhardt's solution (Sambrook et al., 1989), 0.5% SDS and 100 μg/ml of denatured sonicated salmon sperm DNA (Sambrook et al., 1989), followed by hybridization in the same solution containing a random-primed (Feinberg and Vogelstein, 1983) $^{32}$P-dCTP labelled (specific activity>1×10$^9$ cpm/μg) probe for 12 h at ~45° C. The filter is then washed two times for 30 minutes in 2×SSC, 0.5% SDS at a temperature preferably not higher than 45° C., more preferably not higher than 50° C., even more preferably not higher than 55° C., even more preferably not higher than 60° C., most preferably not higher than 65° C., especially not higher than 70° C., more preferably not higher than 75° C.

A suitable DNA or RNA or an oligonucleotide probe to be used in the hybridization may be prepared on the basis of the DNA sequence shown in SEQ ID No. 1, or on basis of the deduced amino acid sequence shown in SEQ ID No.2.

Immunological Cross-reactivity:

Antibodies to be used in determining immunological cross-reactivity may be prepared by use of a purified transglutaminase. More specifically, antiserum against the transglutaminase of the invention may be raised by immunizing rabbits (or other rodents) according to the procedure described by N. Axelsen et al., Chapter 23, or A. Johnstone and R. Thorpe. Purified immunoglobulins may be obtained from the antisera, for example by salt precipitation (($NH_4$)$_2$SO$_4$), followed by dialysis and ion exchange chromatography, e.g. on DEAE-Sephadex. Immunochemical characterization of proteins may be done either by Outcherlony double-diffusion analysis (O. Ouchterlony), by crossed immunoelectrophoresis (N. Axelsen et al., Chapters 3 and 4), or by rocket immunoelectrophoresis (N. Axelsen et al., Chapter 2).

Media

YPD: 10 g yeast extract, 20 g peptone, H$_2$O to 900 ml. Autoclaved, 100 ml 20% glucose (sterile filtered) added.

YPM: 10 g yeast extract, 20 g peptone, H$_2$O to 900 ml. Autoclaved, 100 ml 20% maltodextrin (sterile filtered) added.

10×Basal salt: 75 g yeast nitrogen base, 113 g succinic acid, 68 g NaOH, H$_2$O ad 1000 ml, sterile filtered.

SC-URA: 100 ml 10×Basal salt, 28 ml 20% casamino acids without vitamins, 10 ml 1% tryptophan, H$_2$O ad 900 ml, autoclaved, 3.6 ml 5% threonine and 100 ml 20% glucose or 20% galactose added.

SC-agar: SC-URA, 20 g/l agar added.

SC-variant agar: 20 g agar, 20 ml 10×Basal salt, H$_2$O ad 900 ml, autoclaved, 10 ml 1% tryptophan, 3.6 ml 5% threonine and 100 ml 20% galactose added.

Compositions of the Invention

Although the useful transglutaminase preparation or the recombinant transglutaminase may be added as such it is preferred that it is formulated into a suitable composition. The transglutaminase to be used industrially may be in any form suited for the use in question, e.g. in the form of a dry powder or granulate, in particular a non-dusting granulate, a liquid, in particular a stabilized liquid, or a protected enzyme. Granulates may be produced, e.g. as disclosed in U.S. Pat. No. 4,106,991 and U.S. Pat. No. 4,661,452, and may optionally be coated by methods known in the art. Liquid enzyme preparations may, for instance, be stabilized by adding nutritionally acceptable stabilizers such as a sugar, a sugar alcohol or another polyol, lactic acid or another organic acid according to established methods. Protected enzymes may be prepared according to the method disclosed in EP 238,216. The enzyme preparation of the invention may also comprise a preservative.

Normally, for inclusion in flour, baking or baked products, meat products, cheese and other milk products, fish products, cosmetics, various gelled food, it may be advantageous that the enzyme preparation is in the form of a dry product, e.g. a non-dusting granulate, whereas for inclusion together with a liquid it is advantageously in a liquid form.

The recombinant transglutaminase and the transglutaminase preparations of the present invention may also be used in baking for improving the development, elasticity and/or stability of dough and/or the volume, crumb structure and/or anti-staling properties of the baked product. Although the transglutaminase may be used for the preparation of dough or baked products prepared from any type of flour or meal (e.g. based on rye, barley, oat or maize) the present transglutaminases have been found to be particularly useful in the preparation of dough or baked products made from wheat or comprising substantial amounts of wheat. The baked products produced with a tranglutaminase of the invention includes bread, rolls, baguettes and the like. For baking purposes the transglutaminase of the invention may be used as the only or major enzymatic activity, or may be used in combination with other enzymes such as a lipase, an amylase, an oxidase (e.g. glucose oxidaase, peroxidase), a laccase and/or a protease.

Preferably, the transglutaminase of the invention, especially the recombinant transglutaminase, is used in flour, dough, baked products, meat products, cheese and other milk products, fish products, cosmetics, and various gelled food products in an amount of between 0.01 and 100 mg per kg, more preferably of between 0.1 and 50 mg per kg, most preferably between 0.5 and 30 mg per kg, especially between 1 and 10 mg per kg.

Further, it is contemplated that the recombinant transglutaminase and the transglutaminase preparations of the present invention also can exhibit glutaminase activity, i.e. are capable of glutamine-specific deamidation. Accordingly, a protein substrate essentially free of lysine or at least with a very low content of lysine may be subjected to deamidation by applying the transglutaminase of the invention, such as protein being e.g. gluten or a gluten hydrolysate. In another aspect of the invention, the transglutaminases of the invention can be useful for treatment of food products containing gluten, e.g. for improvement of the palability or other properties of bread and other baked food products, or for reducing the allergenicity of food products containing gluten or gluten hydrolysates.

The invention is further illustrated in the following non-limiting examples.

EXAMPLE 1

Identification of Transglutaminase Secreting Strains Belonging to Oomycetes

The oomycetes were inoculated into shake flasks by cutting out 4–8 small pieces of mycelium (5 mm×5 mm) from PDA plates (39 g/l potato dextrose agar). The shake flasks contain either SFM-4 (4 g/l meat extract, 4 g/l yeast extract, 40 g/l glucose, 8 g/l tryptone, 0.001 g/l $FeSO_4 \cdot 7H_2O$, 2 tablets/1 EBIOS, pH 7.0), ½BPX (potato meal 25 g/l, barley meal 12.5 g/l, BAN 800 MG 0.013 g/l, Na-casein 2.5 g/l, soy meal 5 g/l, $Na_2HPO4$ 2.25 g/l, pluronic 0.025 ml/l) or FG-4 (soy meal 30 g/l, maltodextrinn 15 g/l, bacto peptone 5 g/l, pluronic 0.2 g/l) medium. The cultures were cultured at 26° C. for 5–7 days with shaking. The resulting culture broths were centrifuged 10 minutes at 2300 g to give cell-free culture broths (transglutaminase preparations).

Transglutaminases have been identified in cell-free culture broths of several Oomycetes using the assay described in detail below. It was not possible to detect these transglutaminase activities using the hydroxamate assay (Folk & Cole) as described by others in screening for microbial transglutaminases (EP 0 481504 A1).

The assay used is a slightly modified version of the original procedure (Curtis & Lorand). The transglutaminase activity is measured as incorporation of [1,4-$^{14}$C]putrescine into α-casein. The detection limit of the C14-putrescine incorporation assay was found to be ¹⁄₂₀ of the detection limit of the hydroxamate assay.

To 20 µl of cell-free culture broth is added 5 µl [1,4-$^{14}$C] putrescine (1.85 MBq/ml in 2% aqueous ethanol; specific activity 4.22 GBq/mmol) and 20 µl α-casein (2% in 50 mM Tris-HCl, 100 mM NaCl, pH 7.5). Incubation takes place for 2 h at room temperature following which 30 µl of the assay mixture is spotted onto a small round Whatman 3MM filter. The filter is immediately put into a basket submerged in cold 10% trichloroacetic acid and washed for 20 min to remove excess radioactivity. After this first wash the filters are washed three times with cold 5% trichloroacetic acid, one time with cold ethanol:acetone (50:50, v:v) and one time with cold acetone. Each of these washes takes place for 5 min. In all washing steps the amount of washing liquid should be at least 5 ml/filter. The washed filters are counted directly in scintillation vials.

Table 1 shows examples of species belonging to Oomycetes that secrete transglutaminases into the growth medium upon cultivation and the determined enzyme activities are shown in terms of units of transglutaminase activity.

TABLE 1

| No. | Genus | species | Units/ml | Medium |
| --- | --- | --- | --- | --- |
| CBS 701.95 | Pythium | irregulare | 0.35 | SFM-4 |
| CBS 702.95 | Pythium | 12 | 2.5 | ½BPX |
| CBS 620.94 | Pythium | periilum/periplocum | 2.5 | SFM-4 |
| CBS 703.95 | Pythium | intermedium | 0.83 | SFM-4 |
| CBS 704.95 | Pythium | sp. | 1.5 | ½BPX |
| | Pythium | torulosum | 0.72 | ½BPX |
| CBS 705.95 | Pythium | ultimum | 0.38 | SFM-4 |
| | Pythium | aphanidermatum | 0.37 | SFM-4 |
| CBS 618.94 | Phytophthora | cactorum | 28.3 | SFM-4 |
| | Phytophthora | palmivora | 5.6 | SFM-4 |
| | Phytophthora | cinnamomi | 4.9 | SFM-4 |
| CBS 651.94 | Phytophthora | cryptogea | 10.0 | FG-4 |

Units: An enzyme activity which incorporates 1 nmol [$^{14}$C]-putrescine per hour is defined as 1 U.

EXAMPLE 2

Casein Polymerization

The ability of the transglutaminase present in *Phytophthora cactorum* culture broth to polymerize α-casein was investigated using SDS polyacrylamide gel electrophoresis (SDS-PAGE).

To 20 µl of *Phytophthora cactorum* culture broth was added 20 µl 1.5% α-casein in 0.2 M Tris-HCl, pH 7.5. The mixture was incubated for 2 h at room temperature. Control samples where the culture broth or the α-casein were substituted with water were incubated in parallel.

SDS-PAGE of 10 µl of each of the three samples clearly showed that only the *Phytophthora cactorum* culture broth converted the α-casein to high molecular weight polymers.

EXAMPLE 3

Activity Dependence in the Presence of Cysteine or $Ca^{2+}$-ions at Different Temperatures The effect of reducing agents such as cysteine and $Ca^{2+}$-ions on the transglutaminase activity at different temperatures was investigated using a modification of the putrescine assay described in example 1.

The transglutaminase preparations were concentrated approximately 10 times using a Macrosep™ concentrator from Filtron. Following the samples were diluted 10 times in either:

a) 50 mM Tris-HCl, 100 mM NaCl, 2 mM EDTA, pH 7.5;
b) 50 mM Tris-HCl, 100 mM NaCl, 2 mM EDTA, 1 mM cysteine, pH 7.5;
c) 50 mM Tris-HCl, 100 mM NaCl, 5 mM $CaCl_2$, pH 7.5; or
d) 50 mM Tris-HCl, 100 mM NaCl, 1 mM cysteine, 5 mM $CaCl_2$, pH 7.5.

For activity determination incubation took place for 1 hour at room temperature, 40° C. and 55° C., respectively.

The tables below show the activity dependencies of the different parameters. The enzyme activities are given in relative activities. The activity obtained in buffer+EDTA at room temperature is set to 100. The activity of transglutaminase is dependent on calcium and in most cases the activity measured in the culture broth is further increased by the presence of cysteine.

| | 50 mM Tris-HCl, 100 mM NaCl, pH 7.5 | | | |
|---|---|---|---|---|
| Temperature | 2 mM EDTA | 2 mM EDTA +1 mM Cys | +5 mM $Ca^{2+}$ | +1 mM Cys +5 mM $Ca^{2+}$ |
| Strain: *Phytophthora cactorum*, CBS 618.94 | | | | |
| Room temp. | 100 | 125 | 986 | 991 |
| 40° C. | 68 | 85 | 1954 | 2350 |
| 55° C. | 70 | 58 | 1073 | 829 |
| Strain: *Phytophthora cryptogea*, CBS 651.94 | | | | |
| Room temp. | 100 | 115 | 1267 | 2527 |
| 40° C. | 69 | 69 | 4372 | 7423 |
| 55° C. | 78 | 143 | 3865 | 5518 |
| Strain: Pythium sp., CBS 702.95 | | | | |
| Room temp. | 100 | 57 | 487 | 991 |
| 40° C. | 0 | 0 | 3216 | 5773 |
| 55° C. | 100 | 96 | 4191 | 5896 |
| Strain: *Pythium irregulare*, CBS 701.95 | | | | |
| Room temp. | 100 | 110 | 87 | 86 |
| 40° C. | 167 | 168 | 462 | 450 |
| 55° C. | 50 | 43 | 130 | 114 |
| Strain: *Pythium ultimum*, CBS 705.95 | | | | |
| Room temp. | 100 | 93 | 107 | 141 |
| 40° C. | 142 | 164 | 416 | 483 |
| 55° C. | 15 | 22 | 89 | 88 |
| Strain: *Pythium intermedium*, CBS 703.95 | | | | |
| Room temp. | 100 | 138 | 459 | 2438 |
| 40° C. | 129 | 142 | 3872 | 6117 |
| 55° C. | 181 | 180 | 733 | 1716 |

EXAMPLE 4 pH Dependency of Oomycetes transglutaminases

The pH dependency of the transglutaminase activity present in the transglutaminase preparation of *Pythium irregulare* (CBS 701.95), Pythium sp. (CBS 702.95), *Pythium periilum* (or *P. periplocum*) (CBS 620.94), *Pythium intermedium* (CBS 703.95), Pythium sp. (CBS 704.95), *Pythium ultimum* (CBS 705.95), *Phytophthora cactorum* (CBS 618.94/IFO 30474) and *Phytophthora cryptogea* (CBS 651.94) was investigated using a modification of the putrescine assay described in example 1.

A 4% α-casein solution was made in 50 mM Tris-HCl, 100 mM NaCl, 5 mM $CaCl_2$, 1 mM cysteine, pH 7.5 and diluted 1:1 in a modified 200 mM Britton-Robinson buffer (0.1M $CH_3COOH$, 0.2 M $H_3BO_3$) at the pH values mentioned below.

For pH dependency determination incubation takes place at room temperature for 1 hour at pH 6.0, 6.5, 7.0, 7.5, 8.0, 8.5 or 9.0, respectively.

The table below shows the pH dependencies of the Oomycetes transglutaminases. The stated enzyme activities are relative activities.

| | pH | | | | | | |
|---|---|---|---|---|---|---|---|
| Strains | 6.0 | 6.5 | 7.0 | 7.5 | 8.0 | 8.5 | 9.0 |
| *Pythium irregulare*, CBS 701.95 | 20 | 24 | 36 | 46 | 62 | 100 | 46 |
| Pythium sp., CBS 702.95 | 9 | 16 | 27 | 31 | 48 | 93 | 100 |
| *Pythium intermedium*, CBS 703.95 | 63 | 90 | 99 | 100 | 95 | 54 | 25 |
| Pythium sp., CBS 704.95 | 23 | 33 | 41 | 72 | 95 | 100 | 78 |
| *Pythium ultimum*, CBS 705.95 | 28 | 62 | 68 | 68 | 100 | 93 | 69 |
| *Phytophthora cactorum*, CBS 618.94 | 28 | 38 | 46 | 59 | 74 | 100 | 92 |
| *Phytophthora cryptogea*, CBS 651.94 | 63 | 78 | 86 | 100 | 99 | 93 | 56 |

EXAMPLE 5

Cloning and Expression of a Transglutaminase from *Phytophthora cactorum*, CBS 618.94 and IFO 30474 mRNA was isolated from *Phytophthora cactorum*, CBS 618.94 and IFO 30474, grown in SFM-4 fermentation medium with agitation to ensure sufficient aeration. Mycelia were harvested after 3–5 days' growth, immediately frozen in liquid nitrogen and stored at −80° C. A library from *P. cactorum*, CBS 618.94 or IFO 30474 consisting of approx. $9 \times 10^5$ individual clones was constructed in *E. coli* as described with a vector background of 1%. Plasmid DNA from some of the pools was transformed into yeast, and 50–100 plates containing 250–400 yeast colonies were obtained from each pool.

Transglutaminase-positive colonies were identified and isolated on agar plates with the 5-(biotinamido)-pentylamine assay. cDNA inserts were amplified directly from the yeast colonies and characterized as described in the Materials and Methods section above. The DNA sequence of the cDNA encoding the transglutaminase is shown in SEQ ID No. 1 and the corresponding amino acid sequence is shown in SEQ ID No. 2.

The cDNA is obtainable from the plasmid in DSM 10256.

Total DNA was isolated from a yeast colony and plasmid DNA was rescued by transformation of *E. coli* as described above. In order to express the transglutaminase in Aspergillus, the DNA was digested with HindIII/XbaI, size fractionated on gel, and a fragment corresponding to the transglutaminase gene was purified. The gene was subsequently ligated to HindIII/XbaI digested pHD414 resulting in the plasmid pA2TG3.

After amplification of the DNA in *E. coli* the plasmid was transformed into *Aspergillus oryzae* as described above.

Test of *A. oryzae* Transformants

Each of the transformants were tested for enzyme activity as described above. Some of the transformants had transglutaminase activity which was significantly larger than the *Aspergillus oryzae* background. This demonstrates efficient expression of the transglutaminase in *Aspergillus oryzae*.

Fed Batch Fermentation

Fermentations were carried out as fed-batch processes with maltose syrup as carbon source and ammonia as nitrogen source. The batch phase was carried out at pH 6.5 and the pH was increased to 7.5 during the fed-batch phase. The temperature was maintained at 34° C. during the entire process.

EXAMPLE 6

Production of the Transglutaminase from *Phytophthora cactorum*, CBS 918.94/IFO 60474

*Phytophthora cactorum*, CBS 618.94/IFO 30474, was inoculated into 8 l SFM-4 medium and cultured with shaking at 26° C. for 7 days. The resulting culture broth was filtered through Miracloth to give 5 l of culture filtrate. The transglutaminase activity in the culture filtrate was 22 units/ml.

EXAMPLE 7

Purification and Characterization of Native and Recombinant *Phytophthora cactorum* Transglutaminase.

Transglutaminase Activity Measured with Putrescine Assay:

The putrescine assay was in principle performed according to Lorand et al.

The reaction mixture contained: 2 μmoles of $CaCl_2$, 1 μmoles of cysteine, 75 nmoles of [$^{14}C$]-putrescine (4.03 GBq/mmol; Amersham), 0.7 mg of α-casein, and 0.6 μg of transglutaminase made up to 1 ml with 0.1 M Tris-HCl, pH 7.9. The incubations were performed at ambient temperature. Aliquots of 30 μl were withdrawn after 60 min of incubation and spotted onto Whatman 3 MM filters (D=2 cm). The filters were immediately put into a basket submerged in ice-cold 10% TCA and washed for 20 min. Following the first wash the filters were washed three times with ice-cold 5% TCA and two times with ice-cold acetone. In each washing step there should be at least 5 ml of washing solution per filter. The filters were dried, put into counting vials containing 8 ml of scintillation fluid (Optiphase, Wallac) and the radioactivity was measured in a Packard Tri-Carb liquid scintillation spectrometer. Each determination was performed in triplicate.

Partially Purification of Native *P. cactorum* Transglutaminase.

The culture broth was germ filtrated and concentrated 5 times by ultrafiltration using a Filtron Minisette membrane with 10 kDa cut off. After dialysis against 20 mM Tris-HCl, pH 8.0 the sample was passed through a Q-Sepharose column equilibrated with 20 mM Tris-HCl, pH 8.0. The transglutaminase was eluted from the column using a linear gradient from 0 to 0.5 M sodium chloride. Fractions with transglutaminase activity (putrescine assay) were pooled and concentrated in an Amicon cell equipped with a 10 kDa Diaflo membrane. This preparation of native transglutaminase was only partially pure.

Purification, Specific Activity and N-terminal Sequencing of Recombinant *P. cactorum* Transglutaminase.

The *Aspergillus oryzae* culture broth was germ filtrated and concentrated 5 times by ultrafiltration using a Filtron Minisette membrane with 10 kDa cut off. After dialysis against 50 mM sodium borate, pH 8.0 the sample was passed through a Q-Sepharose column equilibrated with 50 mM sodium borate, pH 8.0. The transglutaminase was eluted from the column using a linear gradient from 0 to 0.5 M sodium chloride. Fractions that gelate casein were pooled and concentrated in an Amicon cell equipped with a 10 kDa Diaflo membrane.

In *Aspergillus oryzae* the recombinant transglutaminase is produced as two forms and from SDS-PAGE the molecular weights are judged to be 57 kDa and 43 kDa, respectively. The ratio between the two forms is dependent on the fermentation time. Early in the fermentation the 57 kDa form dominates but this form is during the fermentation processed to the low molecular weight form. Both forms of the transglutaminase are catalytically active. The specific activity of the recombinant transglutaminase was determined in the putrescine assay and found to be 3,000 U/mg.

N-terminal amino acid sequencing of the two forms of the transglutaminase revealed that the 57 kDa form has a blocked N-terminal and that the 43 kDa form starts at Leu168, cf. SEQ ID No.2.

The Influence of Calcium and Cysteine on the Activity of Recombinant *P. cactorum* Transglutaminase.

The effect of calcium and cysteine (used as a reducing agent) was investigated in the putresine assay. The results presented below are given as relative activities. The activity obtained in buffer at 25° C. is set to 100.

The activity of the transglutaminase is dependent on calcium and the activity is not further increased by the presence of cysteine as reducing agent.

| Temp. (° C.) | Buffer | 2 mM EDTA | 1 mM Cys | 2 mM $Ca^{2+}$ | 1 mM Cys 2 mM $Ca^{2+}$ |
|---|---|---|---|---|---|
| 25 | 100 | 15 | 180 | 270 | 280 |
| 30 | 105 | 10 | 210 | 430 | 490 |
| 40 | 30 | 10 | 75 | 750 | 780 |
| 55 | 10 | 5 | 75 | 350 | 350 |

The Influence of Calcium and Cysteine on the Gelation of Casein by *P. cactorum* Transglutaminase.

The influence of calcium and cysteine on the gelation of casein was investigated as described below.

The gelation mixture contained 80 mg Hammarsten casein, 2 umoles of calcium, 1 μmole cysteine, and approximately 0.03 mg transglutaminase made up to 1 ml with 0.2 M Tris-HCl, pH 7.5. Following incubation overnight at 37° C. the samples were tempered to ambient temperature and the gelation was judged by visual inspection.

Both native and recombinant transglutaminase are able to gelate casein. Contrary to the native enzyme it is not essential for the recombinant enzyme that cysteine is present as a reducing agent.

|  | Buffer | 1 mM Cys | 2 mM $Ca^{2+}$ | 1 mM Cys + 2 mM $Ca^{2+}$ |
|---|---|---|---|---|
| Recombinant *P. cactorum* | −* | − | +** | + |
| Native *P. cactorum*# | − | − | − | + |

*− designates no visible gelation.
**+ designates the formation of a stable gel
partially purified Temperature Profile of *P. cactorum* Transglutaminase.

The temperature profile was determined using the putrescine assay with 0.1 M sodium borate/acetate buffer, pH 7.9 instead of 0.1 M Tris-HCl, pH 7.9.

As can be seen from the table the temperature optimum for both the native and the recombinant transglutaminase is 45 °C.

| Temp. (°C.) | Native P. cactorum# Relative activity (%) | Recomb. P. cactorum Relative activity (%) |
|---|---|---|
| 25 | 20 | 30 |
| 30 | 40 | 50 |
| 35 | 60 | 60 |
| 40 | 85 | 75 |
| 45 | 100 | 100 |
| 50 | 75 | 85 |
| 55 | 15 | 25 | partially purified.

PH Profile of Recombinant P. cactorum Transglutaminase.

The pH profile was determined using the putrescine assay with 0.1 M sodium borate/acetate buffer.

pH optimum of the recombinant Phytophthora cactorum transglutaminase is found to be at pH 8.5.

| pH | Recombinant P. cactorum Relative activity (%) |
|---|---|
| 6.5* | 10 |
| 7.0 | 15 |
| 7.5 | 35 |
| 8.0 | 45 |
| 8.5 | 100 |
| 9.0 | 85 |
| 9.5 | 80 |

*visible precipitate in the substrate

EXAMPLE 8

Crosslinking of Na-caseinate in Solution Measured by the Viscosity Increase as Function of Time A 9% protein solution was prepared from Na-caseinate (Miprodan 30, MD Foods, Denmark, 87.8% protein). Calcium chloride was dissolved in the solution to a concentration of 5 mM and pH was adjusted to 7.0, using NaOH. The solution was heated to 40° C.

A Haake Viscosimeter, VT 501 (Haake Mess-Technik GmbH, Germany) was prepared for viscosity measurements at 40° C. by sensor system MV1 at speed range H, speed 3.

To the protein solution was added recombinant Phytophthora cactorum transglutaminase, cf. example 7, purified to electrophoretic purity, at a dosage of 0.08% (weight of enzyme/weight of protein). The solution was immediately transferred to the viscosimeter for measurement. The viscosity of a control solution without enzyme addition was subsequently measured.

Results: Viscosity (mPa*s) as function of time:

| Time (minutes) | Caseinate solution + enzyme | Control |
|---|---|---|
| 2.66 | 17.5 | 21 |
| 7.33 | 25.4 | 22.8 |
| 12 | 36.9 | 27.2 |
| 24 | 88.6 | 35 |
| 36 | 186.9 | 41.1 |
| 48 | 355.3 | 47.3 |
| 60 | 800.2 | 50.7 |

The casein solution with enzyme solidified subsequently to a gel within a few minutes, while the viscosity of the control remained constant at 53 mPa*s for 120 minutes.

EXAMPLE 9

Transglutaminase for Gluten Strengthening

The strengthening effect of a given dough conditioner on wheat flour dough or gluten dough may be measured by dynamic rheological measurements. These measurements are able to show the strength of a dough, under oscillation. Both wheat fluor dough and gluten dough are viscoelastic materials. In oscillatory measurements, the viscoelastic properties of a wheat dough and a gluten dough can be divided into two components, the dynamic shear storage modulus G' and the dynamic shear loss modulus G" The ratio of the loss and the storage moduli is numerically equal to the tangent of the viscoelastic phase angle δ. An increase in the storage modulus G' and a decrease in the phase angle δ indicate a stronger and more elastic dough.

The dynamic shear storage modulus G' and the viscoelastic phase angle δ were measured in the gluten from 3 doughs, which were treated with the recombinant transglutaminase described in example δ in two dosages, i.e. 4 mg and 10 mg, respectively. The transglutaminase was added to the flour before dough mixing. The gluten was washed out of the flour dough containing the conditioner after the flour dough had been incubated at 32° C. for 1½ hours. The results of the tests are shown in the table below where the measured values of G' and δ resulting from the inclusion of 4 mg and 10 mg enzyme per kg of flour, respectively, are presented as index values relative to the control dough (index 100) with no transglutaminase inclusion.

| Dosage of transglutaminase | G' Index | δ Index |
|---|---|---|
| 4 mg | 135 | 117 |
| 10 mg | 167 | 131 |

From the results it is surprisingly seen that the storage modulus, G', is significantly higher when transglutaminase is present in the dough compared to control without the enzyme. This indicates that the gluten, and thereby also the dough, is significantly strengthened by the action of the enzyme.

Further, it is shown that the viscoelastic phase angle, δ, is lowered relative to the control when tranglutaminase is present in the dough, indicating that a more elastic rheological property of the gluten and thereby the dough is achieved by the action of the enzyme.

REFERENCES CITED IN THE SPECIFICATION

1. Washizu et al., Bioscience, Biotechnology and Biochemistry Vol. 58, 1994, pages 82–87.
2. Tahekana et al., ibid. Vol. 58, 1994, pages 88–92.
3. Takagi et al., EP-0 481 504 A1.

4. Klein et al., J. Bacteriol. Vol. 174, 1992, pages 2599–2605.
5. Lipman and Pearson, Science 227, 1435 (1985).
6. Hudson, L., and Hay, F., Practical Immunology, Third edition (1989), Blackwell Scientific Publications.
7. Sambrook et al.,*Molecular Cloning: A Laboratory Manual*, 2nd Ed., Cold Spring Harbor, 1989.
8. Folk, J. E. & Cole, P. W. (1966) *J. Biol. Chem.* 241, 5518–5525.
9. Curtis, C. G. & Lorand, L. (1976) *Methods in Enzymology* 45, 177–191.
10. Lorand, L., Campbell-Wilkes, L. K., and Cooperstein, L. (1972) Anal. Biochem., 50, 623–631.
11. Newhook, F. J., Waterhouse, G. M., and Stamps, D. J., 1978: Tabular key to the species of Phytophthora De Bary, Mycological Papers No. 143, CAB, Surrey, England.
12. Waterhouse, G. M., 1967: Key to Pythium Pringsheim, Mycological Papers No. 109, CAB, Surrey, England.
13. Ford et al., *Protein Expression and Purification* 2: 95–107, 1991.
14. Cunningham and Wells, *Science* 244, 1081–1085, 1989.
15. de Vos et al., *Science* 255: 306–312, 1992.
16. Smith et al., *J. Mol. Biol.* 224: 899–904, 1992.
17. Wlodaver et al., *FEBS Lett.* 309: 59–64, 1992.
18. O. Ouchterlony in: *Handbook of Experimental Immunology* (D. M. Weir, Ed.), Blackwell Scientific Publications, 1967, pp. 655–706.
19. N. Axelsen et al. in: *A Manual of Quantitative Immunoelectrophoresis*, Blackwell Scientific Publications, 1973.
20. A. Johnstone and R. Thorpe, *Immunochemistry in Practice*, Blackwell Scientific Publications, 1982, pp. 27–31.
21. Cove, Biochem. Biophys. Acta 113 (1966) 51–56.
22. WO 95/02043.
23. WO 94/14953.
24. Sanger et al. (1977) Proc. Natl. Acad. Sci. U.S.A. 74:5463–5467.
25. Becker and Guarante (1991) Methods Enzymol. 194:182–187.
26. Gubler and Hoffman (1983) Gene 25:263–269.
27. Feinberg, A. P., and Vogelstein, B. (1983) Anal. Biochem. 132, 6–13.

---

What is claimed is:

1. An isolated transglutaminase enzyme comprising an amino acid sequence selected from one of:
   a) the amino acid sequence of SEQ ID NO:2 or
   b) an amino acid sequence encoded by the DNA sequence of SEQ ID NO:1.

2. An isolated transglutaminase enzyme encoded by a DNA sequence obtainable from the plasmid in strain *Escherichia coli* DSM 10256.

3. A polypeptide comprising the amino acid sequence of SEQ ID NO:2 or a fragment thereof that has transglutaminase activity.

4. An isolated transglutaminase enzyme comprising an amino acid sequence selected from the group consisting of:
   a) a) the amino acid sequence of SEQ ID NO:2,
   b) an amino acid sequence having at least 95% identity to the amino acid sequence of SEQ ID NO:2,
   c) an amino acid sequence encoded by a DNA sequence having at least 95% identity to the DNA sequence of SEQ ID NO:1, and
   d) an amino acid sequence encoded by a DNA sequence whose complement hybridizes with the transglutaminase-encoding DNA of SEQ ID NO:1 under the following conditions: presoaking in 5×SSC and prehybridizing for 1 hr. at about 45° C. in a solution of 5×SSC, 5×Denhardt's solution, 0.5% SDS and 100 μg/ml of denatured sonicated salmon sperm DNA, followed by hybridization in the same solution supplemented with $^{32}$P dCTP labeled probe for 12 hours at 45° C., followed by washing in 2×SSC, 0.5% SDS for 30 minutes at a temperature of at least 65° C.

5. The enzyme of claim 4, wherein the enzyme is derived from *Phytophthora cactorum*, CBS 618.94, or IFO 30474, *Phytophthora crytogea*, CBS 651.94, *Pythium peruilum* (or *P. periplocum*), CBS 620.94, *Pythium irregulare*, CBS 701.95, Pythium sp., CBS 702.95, *Pythium interedium*, CBS 703.95, Pythium sp., CBS 704.95, or *Pythium ultimum*, CBS 705.95.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 1901 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Phytophthora cactorum
        (B) STRAIN: CBS 618.94

(ix) FEATURE:
        (A) NAME/KEY: CDS
        (B) LOCATION:46..1765

(xi) SEQUENCE DESCRIPTION: SEQ ID NO: 1:

```
CGACATCGAG AAGATTACAA ACTCATTGTT GCAGGTTTCA CAACC ATG GTC TAC        54
                                                  Met Val Tyr
                                                    1

TCA CCC AGC TCC TAC CTC ATC TCC GCC GCC GTG GCT GCG GTG GCC TTC     102
Ser Pro Ser Ser Tyr Leu Ile Ser Ala Ala Val Ala Ala Val Ala Phe
      5              10                  15

CAG ATT CAG CAA GCG ACT GCC GGA TCG CTG TAC TAC GGG GCG TTC TCC     150
Gln Ile Gln Gln Ala Thr Ala Gly Ser Leu Tyr Tyr Gly Ala Phe Ser
 20              25                  30                  35

GTG TCC GAC ACG GAT GGC AAA ATC AGC AAC GAC TCT CCT CTT GTC GGT     198
Val Ser Asp Thr Asp Gly Lys Ile Ser Asn Asp Ser Pro Leu Val Gly
             40                  45                  50

ACC GAA ATT TCC GAC CAG GAC TGC GCC ATC GAG GTG GAG GTC GAC CCG     246
Thr Glu Ile Ser Asp Gln Asp Cys Ala Ile Glu Val Glu Val Asp Pro
                 55                  60                  65

ACG CTG CCG GAC ATC ACG ACC ATC TCG ACG GTG CCG GTG ACC TAC CCT     294
Thr Leu Pro Asp Ile Thr Thr Ile Ser Thr Val Pro Val Thr Tyr Pro
```

-continued

```
                    70                      75                       80
GAC CTG CTG GCC AAC TTG ACG ACG GCT CCG TCG GAG CCG GTG TTC TCA                342
Asp Leu Leu Ala Asn Leu Thr Thr Ala Pro Ser Glu Pro Val Phe Ser
             85                      90                      95

AAG GTG GGC ACG GTG ATC ATG TCG GAG GAG ACC CCC GCC ACC GAC GCC                390
Lys Val Gly Thr Val Ile Met Ser Glu Glu Thr Pro Ala Thr Asp Ala
100                     105                     110                     115

GAC CAG GAC GCG TAC ATC GAC TCG ACG CTT CCG TGG ATT GGC ACT GGT                438
Asp Gln Asp Ala Tyr Ile Asp Ser Thr Leu Pro Trp Ile Gly Thr Gly
                     120                     125                     130

ACG CCG ACC AAG ACG GGT GTG GAG AAG ACC GCC AAG GAC TGC GCT ACT                486
Thr Pro Thr Lys Thr Gly Val Glu Lys Thr Ala Lys Asp Cys Ala Thr
             135                     140                     145

GGG TGG GAG GAG ACC GCG GCC GGC GAT AAG CTC CAG GAG AAG CTC GAA                534
Gly Trp Glu Glu Thr Ala Ala Gly Asp Lys Leu Gln Glu Lys Leu Glu
             150                     155                     160

AAG AAG CGT CGC CTG GAG GAA AAC ACG AAC AGG GAT ATC GCT AGG CTC                582
Lys Lys Arg Arg Leu Glu Glu Asn Thr Asn Arg Asp Ile Ala Arg Leu
165                     170                     175

GAG GCC TAC TTT GGC ACC AAG ATG GAG ATG ACC CTG AAG GAC CTG CCT                630
Glu Ala Tyr Phe Gly Thr Lys Met Glu Met Thr Leu Lys Asp Leu Pro
180                     185                     190                     195

ACC CAG GGT GTC CAC ACA CCG TCG CCG TGG GCT GGA CCG TAC TGG CCG                678
Thr Gln Gly Val His Thr Pro Ser Pro Trp Ala Gly Pro Tyr Trp Pro
                     200                     205                     210

ACT TAC CAG GAC AGT ATC AAC GTT GTC TGG AGC GAG GGA GAA GCC AGC                726
Thr Tyr Gln Asp Ser Ile Asn Val Val Trp Ser Glu Gly Glu Ala Ser
             215                     220                     225

CCC GCT GAG AAG TAC GCC AAG GCT TTC GGT CTG GAC GTG ACG GAC TTC                774
Pro Ala Glu Lys Tyr Ala Lys Ala Phe Gly Leu Asp Val Thr Asp Phe
             230                     235                     240

ATG GAC AAG GTG TCG AAG GAC AAT GGT GTG GAC TCT CAG AGC AAA CGC                822
Met Asp Lys Val Ser Lys Asp Asn Gly Val Asp Ser Gln Ser Lys Arg
             245                     250                     255

AGA CAG TGC CAG ACT GAC GAG GGA TGC GAG TCC CTT AAC AAC GCC AGC                870
Arg Gln Cys Gln Thr Asp Glu Gly Cys Glu Ser Leu Asn Asn Ala Ser
260                     265                     270                     275

AAG TGC GCC ATT CGT GCC GGC AAG ACC TCG GGC TAC TGC ATC CCG ACG                918
Lys Cys Ala Ile Arg Ala Gly Lys Thr Ser Gly Tyr Cys Ile Pro Thr
                     280                     285                     290

TGG TTC GGG ATC TGC CAC GCT TGG GCC CCG GCT GCC ATT CTC GAG GCA                966
Trp Phe Gly Ile Cys His Ala Trp Ala Pro Ala Ala Ile Leu Glu Ala
             295                     300                     305

GAG CCG ACC TGC CCG GTG ACG CAC AAC GGC GTG ACG TTC CAG CCG ATT               1014
Glu Pro Thr Cys Pro Val Thr His Asn Gly Val Thr Phe Gln Pro Ile
             310                     315                     320

GAC ATC AAG GGG CTG ATC TCG GAC GTC TAC GAT GGC GCA GGT GTG GCA               1062
Asp Ile Lys Gly Leu Ile Ser Asp Val Tyr Asp Gly Ala Gly Val Ala
             325                     330                     335

ACG GTT TTC ACG GGT GCC CGG TAC AAC GGC GGT GAC GAT GCT GCC GAT               1110
Thr Val Phe Thr Gly Ala Arg Tyr Asn Gly Gly Asp Asp Ala Ala Asp
340                     345                     350                     355

GAG TAT GGC CGT CAC ACG AAT GCC GCC TAC CGC GAC CTG AAC CCT GCC               1158
Glu Tyr Gly Arg His Thr Asn Ala Ala Tyr Arg Asp Leu Asn Pro Ala
                     360                     365                     370

TAC TTC CAC ATT GCG TCT GCC AAT ATC CTG GGC AAG CTA AAC GCT ACA               1206
Tyr Phe His Ile Ala Ser Ala Asn Ile Leu Gly Lys Leu Asn Ala Thr
             375                     380                     385

TTT GTT GCT GAC GTC GAC GCC GCC GCA GAA GTG TGG AAC CAG CCC GTG               1254
```

```
Phe Val Ala Asp Val Asp Ala Ala Glu Val Trp Asn Gln Pro Val
            390                 395                 400

CGC GGT TTC AAG GTG TTC GAG CAG ACC GCC ATG TCG CTC GAG GAG GCC      1302
Arg Gly Phe Lys Val Phe Glu Gln Thr Ala Met Ser Leu Glu Glu Ala
405                 410                 415

GCT CAG ACC TTC TAC GGC CTT GAG GAG TAC CCG TGG AAT GCC GCC GCC      1350
Ala Gln Thr Phe Tyr Gly Leu Glu Glu Tyr Pro Trp Asn Ala Ala Ala
420                 425                 430                 435

AAG AGC ATT GTG TAC GTC AAG TCG CGT CTC TCG TGG ATC TTC GAG ACG      1398
Lys Ser Ile Val Tyr Val Lys Ser Arg Leu Ser Trp Ile Phe Glu Thr
                440                 445                 450

TAC ACC GAC GGT GGC CTG GTG GCC TCG GGT GAG ATC AAC CGA TAC ACA      1446
Tyr Thr Asp Gly Gly Leu Val Ala Ser Gly Glu Ile Asn Arg Tyr Thr
            455                 460                 465

ACG GGC AAG TAC TAC TAC TAC CTT CTG GAG CTG GAT GAT GCT GGT GAG      1494
Thr Gly Lys Tyr Tyr Tyr Tyr Leu Leu Glu Leu Asp Asp Ala Gly Glu
        470                 475                 480

ATC ATT GGC GGT GAG TGG GTT TAC GAT TCG GAC AGC GAC CAC CCT GAC      1542
Ile Ile Gly Gly Glu Trp Val Tyr Asp Ser Asp Ser Asp His Pro Asp
485                 490                 495

TTC CTG TGG GTG CCC AAG GCG AAG CCT GCT GCG GAC ACG GTG ACC AGC      1590
Phe Leu Trp Val Pro Lys Ala Lys Pro Ala Ala Asp Thr Val Thr Ser
500                 505                 510                 515

ATT GGC CTG AGC TAC GCG GAC GTG AGC ATG CTT CTG GAG AAA TCC GTC      1638
Ile Gly Leu Ser Tyr Ala Asp Val Ser Met Leu Leu Glu Lys Ser Val
                520                 525                 530

GCT TGC TCC GAC TCC ACT TCG GCT GCC GGC TCC GTG TCG TCC GGA TCG      1686
Ala Cys Ser Asp Ser Thr Ser Ala Ala Gly Ser Val Ser Ser Gly Ser
            535                 540                 545

GTG GGT GAG TCC ACG GAG GCG CCT ACG GAA GTG CCC ACG ACG TCG ACG      1734
Val Gly Glu Ser Thr Glu Ala Pro Thr Glu Val Pro Thr Thr Ser Thr
        550                 555                 560

AGT GCT CCC ACT TCT GGC AGT GGC GCG CTG T AAGTATGTCG CAGCTCGTCT      1785
Ser Ala Pro Thr Ser Gly Ser Gly Ala Leu
565                 570

TCCGTATTTG TCGTTGCACA TGAATGTGTA GCTTCGTTTA GATTGCCAGC               1835

TATTCACAAG AAATGGTTCA AACATGCAC TAAGTTCAAG TTGTAAAAAA                1885

AAAAAAAAAA AAAAAA                                                    1901

(2) INFORMATION FOR SEQ ID NO: 2:

(i) SEQUENCE CHARACTERISTICS:
        (A) LENGTH: 573 amino acids
        (B) TYPE: amino acid
        (D) TOPOLOGY: linear (ii) MOLECULE TYPE: protein (xi) SEQUENCE DESCRIPTION: SEQ ID NO: 2:

Met Val Tyr Ser Pro Ser Ser Tyr Leu Ile Ser Ala Ala Val Ala Ala
1               5                   10                  15

Val Ala Phe Gln Ile Gln Gln Ala Thr Ala Gly Ser Leu Tyr Tyr Gly
            20                  25                  30

Ala Phe Ser Val Ser Asp Thr Asp Gly Lys Ile Ser Asn Asp Ser Pro
        35                  40                  45

Leu Val Gly Thr Glu Ile Ser Asp Gln Asp Cys Ala Ile Glu Val Glu
    50                  55                  60

Val Asp Pro Thr Leu Pro Asp Ile Thr Thr Ile Ser Thr Val Pro Val
65                  70                  75                  80
```

```
Thr Tyr Pro Asp Leu Leu Ala Asn Leu Thr Thr Ala Pro Ser Glu Pro
                85                  90                  95
Val Phe Ser Lys Val Gly Thr Val Ile Met Ser Glu Thr Pro Ala
            100                 105                 110
Thr Asp Ala Asp Gln Asp Ala Tyr Ile Asp Ser Thr Leu Pro Trp Ile
            115                 120                 125
Gly Thr Gly Thr Pro Thr Lys Thr Gly Val Glu Lys Thr Ala Lys Asp
        130                 135                 140
Cys Ala Thr Gly Trp Glu Glu Thr Ala Ala Gly Asp Lys Leu Gln Glu
145                 150                 155                 160
Lys Leu Glu Lys Lys Arg Arg Leu Glu Glu Asn Thr Asn Arg Asp Ile
                165                 170                 175
Ala Arg Leu Glu Ala Tyr Phe Gly Thr Lys Met Glu Met Thr Leu Lys
            180                 185                 190
Asp Leu Pro Thr Gln Gly Val His Thr Pro Ser Pro Trp Ala Gly Pro
            195                 200                 205
Tyr Trp Pro Thr Tyr Gln Asp Ser Ile Asn Val Val Trp Ser Glu Gly
        210                 215                 220
Glu Ala Ser Pro Ala Glu Lys Tyr Ala Lys Ala Phe Gly Leu Asp Val
225                 230                 235                 240
Thr Asp Phe Met Asp Lys Val Ser Lys Asp Asn Gly Val Asp Ser Gln
                245                 250                 255
Ser Lys Arg Arg Gln Cys Gln Thr Asp Glu Gly Cys Glu Ser Leu Asn
            260                 265                 270
Asn Ala Ser Lys Cys Ala Ile Arg Ala Gly Lys Thr Ser Gly Tyr Cys
            275                 280                 285
Ile Pro Thr Trp Phe Gly Ile Cys His Ala Trp Ala Pro Ala Ala Ile
        290                 295                 300
Leu Glu Ala Glu Pro Thr Cys Pro Val Thr His Asn Gly Val Thr Phe
305                 310                 315                 320
Gln Pro Ile Asp Ile Lys Gly Leu Ile Ser Asp Val Tyr Asp Gly Ala
                325                 330                 335
Gly Val Ala Thr Val Phe Thr Gly Ala Arg Tyr Asn Gly Gly Asp Asp
            340                 345                 350
Ala Ala Asp Glu Tyr Gly Arg His Thr Asn Ala Ala Tyr Arg Asp Leu
        355                 360                 365
Asn Pro Ala Tyr Phe His Ile Ala Ser Ala Asn Ile Leu Gly Lys Leu
        370                 375                 380
Asn Ala Thr Phe Val Ala Asp Val Asp Ala Ala Ala Glu Val Trp Asn
385                 390                 395                 400
Gln Pro Val Arg Gly Phe Lys Val Phe Glu Gln Thr Ala Met Ser Leu
                405                 410                 415
Glu Glu Ala Ala Gln Thr Phe Tyr Gly Leu Glu Glu Tyr Pro Trp Asn
            420                 425                 430
Ala Ala Ala Lys Ser Ile Val Tyr Val Lys Ser Arg Leu Ser Trp Ile
            435                 440                 445
Phe Glu Thr Tyr Thr Asp Gly Gly Leu Val Ala Ser Gly Glu Ile Asn
        450                 455                 460
Arg Tyr Thr Thr Gly Lys Tyr Tyr Tyr Leu Leu Glu Leu Asp Asp
465                 470                 475                 480
Ala Gly Glu Ile Ile Gly Gly Trp Val Tyr Asp Ser Asp Ser Asp
                485                 490                 495
```

―continued

```
His Pro Asp Phe Leu Trp Val Pro Lys Ala Lys Pro Ala Ala Asp Thr
            500                 505                 510

Val Thr Ser Ile Gly Leu Ser Tyr Ala Asp Val Ser Met Leu Leu Glu
            515                 520                 525

Lys Ser Val Ala Cys Ser Asp Ser Thr Ser Ala Ala Gly Ser Val Ser
    530                 535                 540

Ser Gly Ser Val Gly Glu Ser Thr Glu Ala Pro Thr Glu Val Pro Thr
545                 550                 555                 560

Thr Ser Thr Ser Ala Pro Thr Ser Gly Ser Gly Ala Leu
                565                 570
```